(12) United States Patent
Shirakawa et al.

(10) Patent No.: US 10,175,597 B2
(45) Date of Patent: Jan. 8, 2019

(54) LIQUID DEVELOPER AND METHOD OF PRODUCING SAME

(71) Applicant: CANON KABUSHIKI KAISHA, Tokyo (JP)

(72) Inventors: Jun Shirakawa, Kawaguchi (JP); Junji Ito, Hiratsuka (JP); Yasuhiro Aichi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/559,580

(22) PCT Filed: May 27, 2016

(86) PCT No.: PCT/JP2016/066516
§ 371 (c)(1),
(2) Date: Sep. 19, 2017

(87) PCT Pub. No.: WO2016/190450
PCT Pub. Date: Dec. 1, 2016

(65) Prior Publication Data
US 2018/0046106 A1  Feb. 15, 2018

(30) Foreign Application Priority Data

May 27, 2015  (JP) ................................. 2015-107395

(51) Int. Cl.
| G03G 9/135 | (2006.01) |
| C07F 9/09 | (2006.01) |
| C07F 9/10 | (2006.01) |
| G03G 9/125 | (2006.01) |
| G03G 9/13 | (2006.01) |
| C08F 120/68 | (2006.01) |
| G03G 9/08 | (2006.01) |

(52) U.S. Cl.
CPC ........... *G03G 9/1355* (2013.01); *C07F 9/091* (2013.01); *C07F 9/106* (2013.01); *C08F 120/68* (2013.01); *G03G 9/0804* (2013.01); *G03G 9/125* (2013.01); *G03G 9/13* (2013.01); *G03G 9/131* (2013.01)

(58) Field of Classification Search
CPC ...... G03G 9/131; G03G 9/125; G03G 9/1355; G03G 9/135; G03G 9/13; G03G 9/12; G03G 9/133
USPC ..................... 430/115, 114, 116, 112, 137.22
See application file for complete search history.

(56) References Cited

U.S. PATENT DOCUMENTS

| 5,300,390 A * | 4/1994 | Landa ..................... G03G 9/132 430/115 |
| 5,364,726 A | 11/1994 | Morrison et al. |
| 5,395,724 A | 3/1995 | Morrison et al. |
| 5,622,804 A * | 4/1997 | Matsuoka ................ G03G 9/12 430/115 |
| 5,783,350 A | 7/1998 | Matsuoka et al. |
| 7,582,604 B2 | 9/2009 | Vrijbloed et al. |
| 8,158,321 B2 | 4/2012 | Teishev et al. |
| 8,399,170 B2 | 3/2013 | Iwase et al. |
| 9,740,118 B2 * | 8/2017 | Hasegawa ............ G03G 9/0806 |
| 9,766,568 B2 | 9/2017 | Ito et al. |
| 9,798,265 B2 * | 10/2017 | Inoue ..................... G03G 9/131 |
| 2010/0136474 A1 | 6/2010 | Iwase et al. |
| 2015/0192875 A1 | 7/2015 | Ito et al. |
| 2016/0349651 A1 | 12/2016 | Ito et al. |
| 2016/0349652 A1 | 12/2016 | Natori et al. |
| 2016/0349653 A1 | 12/2016 | Tanabe et al. |
| 2016/0349655 A1 | 12/2016 | Natori et al. |
| 2016/0349656 A1 | 12/2016 | Hasegawa et al. |
| 2017/0090325 A1 | 3/2017 | Tanabe et al. |

(Continued)

FOREIGN PATENT DOCUMENTS

| JP | H04-336543 | 11/1992 |
| JP | H11-344841 | 12/1999 |
| JP | 2003241439 | 8/2003 |

(Continued)

OTHER PUBLICATIONS

Japanese Patent Office J-PlatPat machine-assisted English-language translation of JP 2016-224405 A (pub. Dec. 2016).*

(Continued)

*Primary Examiner* — Janis L Dote
(74) *Attorney, Agent, or Firm* — Venable LLP

(57) ABSTRACT

Provided is a liquid developer that gives a high image density, has a high resistance, suppresses the appearance of image blurring, can be reused, is readily cured by ultraviolet radiation, and can accommodate higher process speeds. This liquid developer contains a carrier liquid, a toner particle insoluble in the carrier liquid, and a compound with the following formula (1)

formula (1)

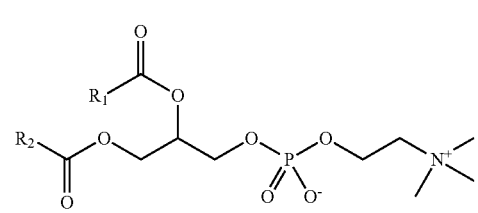

[In formula (1), $R_1$ and $R_2$ each independently represent an alkyl group having at least 13 and not more than 23 carbons.].

17 Claims, No Drawings

(56) References Cited

U.S. PATENT DOCUMENTS

2017/0102628 A1   4/2017   Kabashima et al.

FOREIGN PATENT DOCUMENTS

| | | |
|---|---|---|
| JP | 2009-503579 | 1/2009 |
| JP | 2009-175242 | 8/2009 |
| JP | 20160130012 | 7/2016 |
| JP | 2016-224405 A * | 12/2016 |
| WO | 2006/126566 | 11/2006 |
| WO | 2007/000974 | 1/2007 |
| WO | 2007/000975 | 1/2007 |
| WO | 2007/018503 | 2/2007 |
| WO | 2007/108485 | 9/2007 |

OTHER PUBLICATIONS

Written Opinion of the International Searching Authority (Form PCT/ISA/237) in PCT/JP2016/065516, dated Sep. 6, 2016.*
Industrial Organic Pigments, Willy Herbst, Klaus Hunger Copyright c 2004 Wiley-VCH Verlag GmbH & Co. KGaA, Weinheim, Third Edition. pp. 637-645.
U.S. Appl. No. 15/549,484, filed Aug. 8, 2017, Hiroshi Tanabe.
U.S. Appl. No. 15/559,876, filed Sep. 20, 2017, Hiroshi Tanabe.

* cited by examiner

LIQUID DEVELOPER AND METHOD OF PRODUCING SAME

TECHNICAL FIELD

The present invention relates to a liquid developer used in image-forming apparatuses that utilize an electrophotographic system such as electrophotography, electrostatic recording, electrostatic printing. The present invention also relates to a method of producing this liquid developer.

BACKGROUND ART

An electrophotographic system is a method in which printed material is obtained by uniformly charging the surface of an image bearing member such as a photosensitive member (charging step), forming an electrostatic latent image on the surface of the image bearing member by photoexposure (photoexposure step), developing the formed electrostatic latent image with a developer formed of colored resin particles (development step), transferring the developer image to a recording medium such as paper or plastic film (transfer step), and fixing the transferred developer image to the recording medium (fixing step).

The developers here are broadly classified into dry developers and liquid developers: colored resin particles constituted of a material that contains a binder resin and a colorant such as a pigment are used in a dry state in the former, while the colored resin particles are dispersed in an electrically insulating liquid in the latter.

The need for color output and high-speed printing from image-forming apparatuses that use an electrophotographic system, e.g., copiers, facsimile machines, printers, and so forth, has been increasing in recent years. Within the realm of color printing, the demand for high-resolution, high-quality images has resulted in demand for developers that can accommodate high-speed printing while having the ability to form high-resolution, high-quality images.

Liquid developers are known to be developers that offer advantages with regard to color image reproducibility. With a liquid developer, the occurrence of aggregation by the colored resin particles in the liquid developer is suppressed during storage, and due to this a microfine toner particle can be used. As a consequence, excellent properties with regard to the reproducibility of fine line images and the reproducibility of gradations are readily obtained with a liquid developer. Development is becoming quite active with regard to high-image-quality, high-speed digital printing apparatuses that exploit these excellent features by utilizing electrophotographic technologies that use liquid developers. In view of these circumstances, there is demand for the development of liquid developers that have even better properties.

Investigations have been carried out into the addition of lecithin to liquid developers in order to bring about electrophoresis-mediated development by and transfer of the developer through the stable dispersion and charging of the toner particles in the carrier liquid.

For example, PTL 1 indicates that lecithin effectively acts as an amphoteric emulsifying agent. PTL 2, on the other hand, indicates that the generation of charge on the toner particle is promoted by the addition of lecithin as a charging regulator. In addition, PTL 3 indicates that lecithin is a charge control agent.

CITATION LIST

Patent Literature

[PTL 1] Japanese Patent Application Laid-open No. 2009-175242
[PTL 2] Japanese Patent Application Laid-open No. H4-336543
[PTL 3] Japanese Translation of PCT Application No. 2009-503579

SUMMARY OF INVENTION

Technical Problem

However, when lecithin is added to a liquid developer in order to improve the toner particle dispersibility and charging performance, the volume resistivity of the liquid developer undergoes a large decline in comparison to that of a lecithin-free liquid developer and it then becomes difficult to obtain a high image density. In addition, the decline in the volume resistivity of the liquid developer brought about by the addition of lecithin facilitates the appearance of image blurring and causes the developing performance to deteriorate.

On the other hand, the redispersion of the toner particles in the liquid developer is crucial when a liquid developer is subjected to repeated use, but an unsatisfactory ability to inhibit toner particle aggregation has been a problem with lecithin.

In addition, when the liquid developer is an ultraviolet-curable liquid developer, the lecithin dissolved in the carrier liquid inhibits the ultraviolet-induced curing reaction.

Given the preceding, there is demand for the development of a compound that prevents the decline in the volume resistivity of the liquid developer, has a high ability to impart charge to toner particles, has the ability to inhibit toner particle aggregation, and does not inhibit ultraviolet-induced curing reactions.

Thus, the present invention, by providing a liquid developer that contains such a compound, enables liquid developer reuse and realizes faster process speeds while producing a high image density and suppressing the appearance of image blurring.

Solution to Problem

The present invention is a liquid developer that contains a carrier liquid, a toner particle insoluble in the carrier liquid, and a compound with the following formula (1)

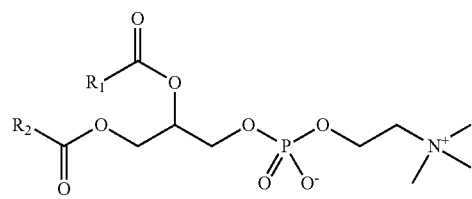

formula (1)

[In formula (1), $R_1$ and $R_2$ each independently represent an alkyl group having at least 13 and not more than 23 carbons.].

The present invention is also a method of producing a liquid developer, that includes a step of applying a shear force and/or a step of applying a heat treatment, to a mixture in which the carrier liquid, the toner particle insoluble in the carrier liquid, and the compound with formula (1) are mixed.

Advantageous Effects of Invention

The present invention can provide a liquid developer that is reusable, that can accommodate faster process speeds, and that produces a high image density while suppressing the appearance of image blurring.

DESCRIPTION OF EMBODIMENTS

The present invention is described in detail in the following.

The liquid developer of the present invention contains a carrier liquid, a toner particle insoluble in the carrier liquid, and a compound with formula (1).

The individual constituent components present in the liquid developer of the present invention are described in the following.

The liquid developer of the present invention contains a compound with the following formula (1) (this compound is also referred to below simply as compound 1).

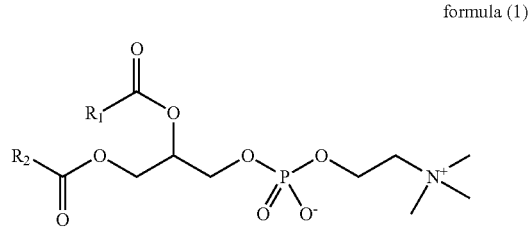

formula (1)

$R_1$ and $R_2$ in formula (1) each independently represent an alkyl group having at least 13 and not more than 23 carbons and preferably represent an alkyl group having at least 15 and not more than 21 carbons. This alkyl group is preferably a linear-chain alkyl group.

When $R_1$ and $R_2$ are alkyl groups having not more than 23 carbons, the polarity of the molecule then does not become too low and a decline in the adsorbability to the toner particle is suppressed, the electrophoretic mobility of the toner particle is improved, the decline in the volume resistivity of the liquid developer is prevented, and excellent developing characteristics are obtained. In addition, acquisition in this case is easy and relatively inexpensive.

When, on the other hand, $R_1$ and $R_2$ are alkyl groups having at least 13 carbons, the polarity of the molecule then does not become too high and the formation in the carrier liquid of particles formed of only compound 1 is suppressed and compound 1 readily becomes oriented at the toner particle surface. As a result, the electrophoretic mobility of the toner particle is improved and the decline in the volume resistivity of the liquid developer is prevented and excellent developing characteristics are then obtained. In addition, an adequate steric hindrance effect by compound 1 is obtained and an excellent toner particle redispersibility in the liquid developer then occurs.

This compound 1 can be produced by carrying out a hydrogenation treatment on the various lecithins to convert the fatty acid bonded in the lecithin to a saturated fatty acid.

On the other hand, a commercial hydrogenated lecithin may be used as a mixture that contains this compound 1 in high concentrations.

Commercial hydrogenated lecithins can be exemplified by BASIS LP-20H and BASIS LS-60HR (The Nisshin OilliO Group, Ltd.); LECINOL S-10, LECINOL S-10E, LECINOL S-10EX, LECINOL S-10M, LECINOL S-GF, and LECINOL S-PIE (Nikko Chemicals Co., Ltd.); and SLP-PC70HS, SLP-PC92H, and SLP-White H (Tsuji Oil Mills Co., Ltd.).

As described above, through the use of compound 1, the electrophoretic mobility of the toner particle is improved, the decline in the volume resistivity of the liquid developer is prevented, and an excellent developing performance is obtained. In addition, the toner particle redispersibility, which is crucial when the liquid developer is subjected to repeated reuse, also becomes excellent.

In addition to the preceding, the use of compound 1 makes it possible to avoid an inhibition of the ultraviolet-induced curing reaction when the liquid developer is an ultraviolet-curable liquid developer and thereby enables fixing to occur at a low ultraviolet dose.

The reason is unclear as to why the use of compound 1 yields better properties than the use of lecithin. The following, however, is hypothesized.

The fatty acid segment of lecithin is frequently an alkenyl group that has one double bond among the carbon-carbon bonds in its carbon skeleton, and as a consequence there is a lower degree of freedom for intramolecular motion than for compound 1, in which the fatty acid segment is not an alkenyl group. Due to this, the van der Waals forces acting between the molecules constituting lecithin are weak and dissolution in various solvents readily occurs. The present inventors hypothesize that this ready solubility by lecithin causes a reduction in the amount of charge accompanying a reduction in the adsorption rate by lecithin to the toner particle, and a reduction in redispersibility caused by toner particle aggregation, a reduction in the volume resistivity of the carrier liquid, and the occurrence of inhibition of the ultraviolet-induced curing reaction, with a deterioration in the characteristics being the result.

The content of compound 1 in the liquid developer of the present invention is not particularly limited, but, expressed per 100 mass parts of the toner particle, is preferably at least 0.10 mass parts and not more than 10.00 mass parts and is more preferably at least 0.50 mass parts and not more than 5.00 mass parts. It is even more preferably at least 1.00 mass parts and not more than 3.00 mass parts and is particularly preferably at least 1.50 mass parts and not more than 2.00 mass parts.

The liquid developer of the present invention may contain, in combination with compound 1, a polymer compound having a structural unit with the following formula (2) (this polymer compound is also referred to below simply as polymer compound 2). This polymer compound 2 also acts as a charge control agent.

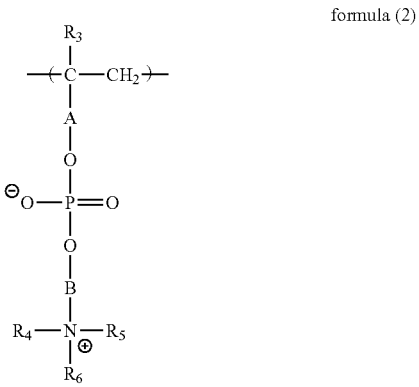

formula (2)

In formula (2), $R_3$ to $R_6$ each independently represent either of a hydrogen atom and an alkyl group; A represents any of a single bond, carbonyl group, alkylene group, arylene group, and —$COOR_9$— (wherein the carbonyl group in —$COOR_9$— is bonded to a carbon atom to which $R_3$ is bonded and $R_9$ represents an alkylene having at least 1 and not more than 4 carbons); and B represents either of an alkylene group and an arylene group.

The alkyl group for $R_3$ in formula (2) is preferably a $C_{1-4}$ alkyl group. It can be exemplified by the methyl group, ethyl group, n-propyl group, isopropyl group, and n-butyl group.

$R_3$ in formula (2) may be freely selected from the hydrogen atom and the substituents indicated above, but the hydrogen atom and methyl group are preferred from the standpoint of the production (polymerizability) of the polymer compound.

The alkyl group for $R_4$ to $R_6$ in formula (2) is preferably a $C_{1-18}$ alkyl group. Examples here are the methyl group, ethyl group, n-propyl group, isopropyl group, n-butyl group, n-octyl group, 2-ethylhexyl group, dodecyl group, and octadecyl group. These alkyl groups may additionally be substituted and may be bonded to each other to form a ring.

The A in formula (2) is a linking group that bonds the polymer main chain to the phosphate ester segment, and it represents any of a carbonyl group, alkylene group, arylene group, and —$COOR_9$— (wherein the carbonyl group in —$COOR_9$— is bonded to the carbon atom to which $R_3$ is bonded and $R_9$ represents an alkylene having at least 1 and not more than 4 carbons). Direct bonding to the polymer main chain may also proceed through a single bond.

The alkylene group encompassed by the linking group A may be linear chain or branched, and a $C_{1-4}$ alkylene group is preferred.

Examples here are the methylene group, ethylene group, propylene group, and the various butylene groups.

The arylene group encompassed by the linking group A can be exemplified by the 1,2-phenylene group, 1,3-phenylene group, 1,4-phenylene group, naphthalene-1,4-diyl group, naphthalene-1,5-diyl group, and naphthalene-2,6-diyl group.

With regard to the —$COOR_9$— encompassed by the linking group A, the carbonyl in this —$COOR_9$— is bonded to the carbon atom to which $R_3$ is bonded, and $R_9$ is alkylene having at least 1 and not more than 4 carbons. This alkylene may be linear chain or branched.

These linking groups may also be substituted, and this substitution should not cause a substantial reduction in the charging characteristics of the polymer compound but is not otherwise particularly limited.

While the linking group A is not particularly limited as described above, the carbonyl group and —$COOR_9$— (wherein the carbonyl group in —$COOR_9$— is bonded to the carbon atom to which $R_3$ is bonded and $R_9$ represents an alkylene having at least 1 and not more than 4 carbons) are more preferred from the standpoint of the ease of starting material acquisition and the ease of production.

B in formula (2) is a linking group that bonds the quaternary ammonium segment to the phosphate ester segment and represents either of an alkylene group and an arylene group.

The alkylene group encompassed by the linking group B may be linear chain or branched, and a $C_{1-4}$ alkylene group is preferred.

Examples here are the methylene group, ethylene group, propylene group, and the various butylene groups.

The arylene group encompassed by the linking group B can be exemplified by the 1,2-phenylene group, 1,3-phenylene group, 1,4-phenylene group, naphthalene-1,4-diyl group, naphthalene-1,5-diyl group, and naphthalene-2,6-diyl group.

These linking groups may also be substituted, and this substitution should not cause a substantial reduction in the charging characteristics of the polymer compound but is not otherwise particularly limited.

While the linking group B is not particularly limited as described above, simple alkylene groups such as the methylene group and ethylene group are more preferred from the standpoint of the ease of starting material acquisition and the ease of production.

In the present invention, the polymer compound 2 may be a polymer compound formed of a copolymer having a structural unit with formula (2) and a structural unit with the following formula (3) (this polymer compound is also referred to below simply as polymer compound 3). Polymer compound 3 also acts as a charge control agent.

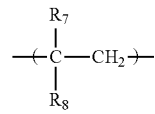

formula (3)

[In formula (3), $R_7$ represents either of a hydrogen atom and an alkyl group, and $R_8$ represents any of an alkyl group, carboxylate ester group, carboxamide group, alkoxy group, and aryl group.]

The alkyl group for $R_7$ in formula (3) is preferably a $C_{1-4}$ alkyl group. It can be exemplified by the methyl group, ethyl group, n-propyl group, isopropyl group, and n-butyl group.

$R_7$ in formula (3) may be freely selected from the hydrogen atom and the substituents indicated above, but the hydrogen atom and methyl group are preferred from the standpoint of the production (polymerizability) of the copolymer.

The alkyl group for $R_8$ in formula (3) is preferably a $C_{1-30}$ alkyl group. Examples here are the methyl group, ethyl group, n-propyl group, n-butyl group, n-hexyl group, n-decyl group, n-hexadecyl group, octadecyl group, docosyl group, and triacontyl group.

The aryl group for $R_8$ in formula (3) can be exemplified by aryl groups such as the phenyl group, 1-naphthyl group, and 2-naphthyl group.

The carboxylate ester group for $R_8$ in formula (3) can be exemplified by —$COOR_{10}$ (wherein $R_{10}$ represents any of a $C_{1-30}$ alkyl group, the phenyl group, and a $C_{1-30}$ hydroxyalkyl group). Specific examples are ester groups such as the methyl ester group, ethyl ester group, n-propyl ester group, isopropyl ester group, n-butyl ester group, tert-butyl ester group, octyl ester group, 2-ethylhexyl ester group, dodecyl ester group, octadecyl ester group, docosyl ester group, triacontyl ester group, phenyl ester group, and 2-hydroxyethyl ester group.

The carboxamide group for $R_8$ in formula (3) can be exemplified by —CO—$NR_{11}R_{12}$ (wherein $R_{11}$ and $R_{12}$ each independently represent any of hydrogen, $C_{1-30}$ alkyl groups, and the phenyl group). Specific examples are amide groups such as the N-methylamide group, N,N-dimethylamide group, N,N-diethylamide group, N-isopropylamide group, N-tert-butylamide group, N-n-decylamide group, N-n-hexadecylamide group, N-octadecylamide group, N-docosylamide group, N-triacontylamide group, and N-phenylamide group.

The alkoxy group for $R_8$ in formula (3) can be exemplified by $C_{1-30}$ alkoxy groups and $C_{1-30}$ hydroxyalkoxy groups. Specific examples are alkoxy groups such as the methoxy group, ethoxy group, n-propoxy group, isopropoxy group, n-butoxy group, n-hexyloxy group, cyclohexyloxy group, n-octyloxy group, 2-ethylhexyloxy group, dodecyloxy group, octadecyloxy group, docosyloxy group, triacontyloxy group, and 2-hydroxyethoxy group.

The $R_8$ substituent in formula (3) may also be substituted, and this substitution should not cause a substantial reduction in the charging characteristics of the copolymer but is not otherwise particularly limited. The substituents that may be introduced in this case can be exemplified by alkoxy groups such as the methoxy group and ethoxy group, amino groups such as the N-methylamino group and N,N-dimethylamino group, acyl groups such as the acetyl group, and halogen atoms such as the fluorine atom and chlorine atom.

The $R_7$ and $R_8$ in formula (3) may be freely selected from the substituents indicated above, but appropriate substituents should be selected in conformity to the application for which the copolymer will be used.

In the present invention, the copolymerization compositional ratio for this copolymer is not particularly limited, but the molar ratio of the structural unit with formula (2) to the structural unit with formula (3) is preferably 0.01:99.99 to 50:50 and is more preferably 1:99 to 30:70.

The weight-average molecular weight (Mw) of the polymer compound having the structural unit with formula (2) is not particularly limited, but this weight-average molecular weight (Mw) is preferably approximately at least 3,000 and not more than 300,000, more preferably at least 3,000 and not more than 150,000, even more preferably at least 3,000 and not more than 50,000, and particularly preferably at least 3,000 and not more than 20,000.

In the present invention, the content ratio on a molar basis of the compound with formula (1) to the polymer compound having the structural unit with formula (2) in the liquid developer is not particularly limited but is preferably 5:1 to 35:1 and is more preferably 7:1 to 35:1.

There are no particular limitations on the method of producing this polymer compound as long as a polymer compound with the structure described above is obtained, and, for example, production can be carried out by the following methods.

Thus, production can be carried out by (i) a method in which a vinyl monomer corresponding to formula (2) is produced followed by production by its polymerization, and (ii) a method in which a polymer compound corresponding to the polymer main chain of formula (2) is synthesized followed by bonding the zwitterion segment of formula (2) by a polymer reaction.

On the other hand, for example, use may be made of a commercial phospholipid polymer as a mixture that contains the polymer compound 3 in high concentrations. Lipidure (registered trademark)-S (NOF Corporation) is an example of a commercial phospholipid polymer.

The content of the polymer compound having the structural unit with formula (2) in the liquid developer of the present invention is not particularly limited, but, expressed per 100 mass parts of the toner particle, it is preferably at least 0.01 mass parts and not more than 10.00 mass parts and is more preferably at least 0.05 mass parts and not more than 5.00 mass parts. It is more preferably at least 0.10 mass parts and not more than 3.00 mass parts and is particularly preferably at least 0.30 mass parts and not more than 2.00 mass parts.

[The carrier liquid]

In the present invention, the carrier liquid should be a liquid that exhibits a high volume resistivity, electrical insulating properties, and a low viscosity around room temperature, but is not otherwise particularly limited.

In addition, the carrier liquid is preferably selected from liquids that do not dissolve the binder resin that is incorporated in the toner particle.

In specific terms, it is preferably selected from carrier liquid/binder resin combinations for which not more than 1 mass part of the binder resin dissolves at a temperature of 25° C. in 100 mass parts of the carrier liquid. When the solubility of the binder resin exceeds this, a trend is assumed wherein toner particle formation is impaired.

Specific examples of the carrier liquid are hydrocarbon solvents such as hexane, heptane, and octane; liquid paraffin solvents such as ISOPAR G® synthetic isoparaffinic fluid, ISOPAR E®, and ISOPAR L® (Exxon Mobil Corporation) and MORESCO White P-40 and MORESCO White MT-30P (Moresco Corporation); and silicone compounds.

The volume resistivity of the carrier liquid is preferably at least $1 \times 10^9$ Ω·cm and not more than $1 \times 10^{15}$ Ω·cm and is more preferably at least $1 \times 10^{10}$ Ω·cm and not more than $1 \times 10^{15}$ Ω·cm.

A volume resistivity of less than $1 \times 10^9$ Ω·cm facilitates a drop in the potential of the electrostatic latent image and sets up a trend of impeding the generation of a high optical density and/or a trend of facilitating the occurrence of image blurring.

The viscosity of the carrier liquid at 25° C., on the other hand, is preferably at least 0.5 mPa·s and less than 100 mPa·s and is more preferably at least 0.5 mPa·s and less than 20 mPa·s. An excessively high viscosity facilitates a decline in the electrophoretic mobility of the toner particle and sets up a declining trend for the print speed.

A liquid polymerizable compound can also be used for the carrier liquid in order to make the liquid developer of the present invention into a curable liquid developer.

Liquid polymerizable compounds that can be used should satisfy the characteristics indicated above for the carrier liquid but are not otherwise particularly limited.

In addition, the liquid polymerizable compound may be a component capable of undergoing polymerization brought about by a photopolymerization reaction.

The photopolymerization reaction may be a reaction induced by any type of light, but reactions induced by ultraviolet radiation are preferred. That is, the carrier liquid may be an ultraviolet-curable liquid polymerizable compound.

Liquid polymerizable compounds include, for example, liquid polymerizable compounds having a radical polymerizability, liquid polymerizable compounds having a cationic polymerizability, and liquid polymerizable compounds having both capabilities, and any of these can be used as appropriate.

Examples here are vinyl ether compounds, urethane compounds, styrenic compounds, and acrylic compounds as well as cyclic ether compounds such as epoxy compounds and oxetane compounds.

In the present invention, a single one of these compounds may be used by itself as the liquid polymerizable compound or a combination of two or more may be used.

In the present invention, a liquid cationically polymerizable compound is preferably incorporated as the liquid polymerizable compound, and the incorporation of a vinyl ether compound is more preferred.

The use of a vinyl ether compound makes it possible to obtain an ultraviolet-curable liquid developer that exhibits a high volume resistivity, a low viscosity, and a high sensitivity.

The present inventors hypothesize that this expression of favorable characteristics is caused by the small intramolecular polarization of the electron density in vinyl ether compounds.

Here, the vinyl ether compound refers to a compound that has a vinyl ether structure (—CH=CH—O—C—).

This vinyl ether structure is preferably given by R—CH=CH—O—C— (R is hydrogen or $C_{1-3}$ alkyl and is preferably hydrogen or methyl).

Acrylic polymerizable compounds and cyclic ether polymerizable compounds, e.g., epoxides and oxetanes, are also widely used as the aforementioned liquid cationically polymerizable compound. However, acrylic polymerizable compounds exhibit intramolecular polarization of the electron density and, due to the operation of intermolecular electrostatic interactions, it is difficult for a low viscosity to appear and a declining trend is assumed for the volume resistivity.

With cyclic ether polymerizable compounds, on the other hand, it also difficult to obtain a high volume resistivity and in addition the polymerization reaction rate tends to be lower than for vinyl ether compounds.

In one preferred embodiment in the present invention, the vinyl ether compound is also a compound that does not contain a heteroatom outside the vinyl ether structure.

Here, "heteroatom" denotes an atom other than the carbon atom and hydrogen atom.

When it is a compound that does not contain a heteroatom outside the vinyl ether structure, intramolecular polarization of the electron density is suppressed and a high volume resistivity is readily obtained.

In another preferred embodiment in the present invention, the vinyl ether compound also preferably does not contain a carbon-carbon double bond outside of the vinyl ether structure in the vinyl ether compound. Polarization of the electron density is suppressed and a high volume resistivity is readily obtained with a vinyl ether compound that does not contain a carbon-carbon double bond outside of the vinyl ether structure.

The vinyl ether compound is preferably given by the following formula (C) in the present invention.

$$(H_2C=CH-O)_n-R \qquad \text{formula (C)}$$

[In formula (C), n represents the number of vinyl ether structures in one molecule and is an integer from 1 to 4. R is an n-valent hydrocarbon group.]

n is preferably an integer from 1 to 3.

R preferably is a group selected from $C_{1-20}$ linear-chain or branched, saturated or unsaturated aliphatic hydrocarbon groups, $C_{5-12}$ saturated or unsaturated alicyclic hydrocarbon groups, and $C_{6-14}$ aromatic hydrocarbon groups, and these alicyclic hydrocarbon groups and aromatic hydrocarbon groups may have a $C_{1-4}$ saturated or unsaturated aliphatic hydrocarbon group.

R is more preferably a $C_{4-18}$ linear-chain or branched saturated aliphatic hydrocarbon group.

Specific examples of vinyl ether compounds are given below (example compounds A-1 to A-30), but the present invention is not limited to these examples.

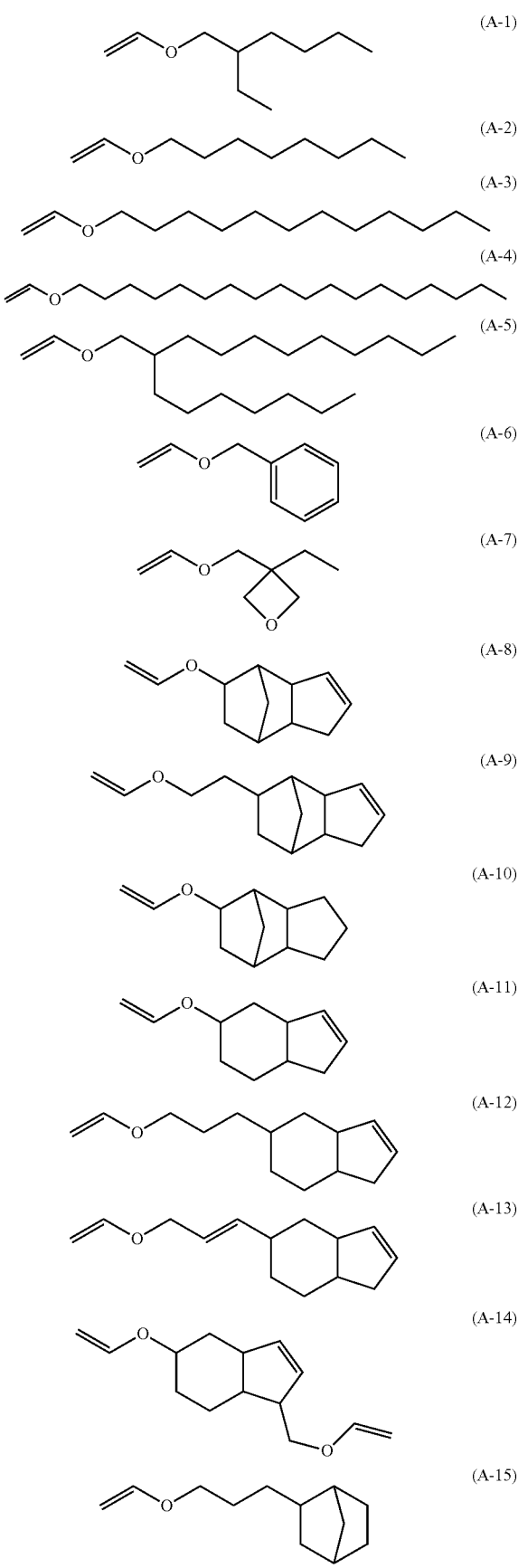

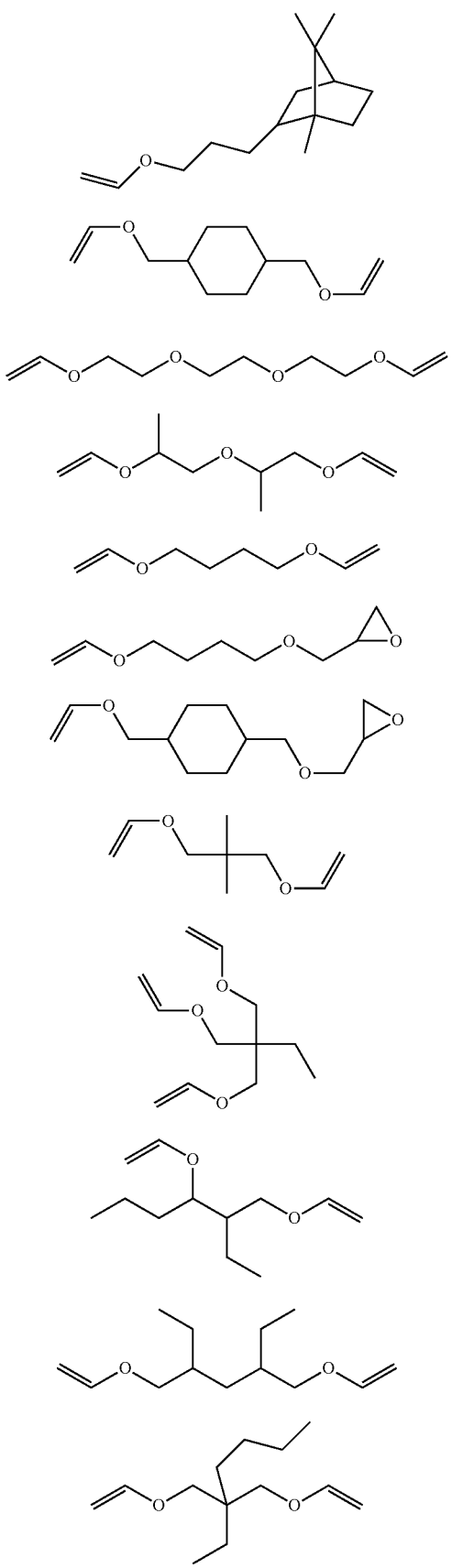

(A-16)
(A-17)
(A-18)
(A-19)
(A-20)
(A-21)
(A-22)
(A-23)
(A-24)
(A-25)
(A-26)
(A-27)

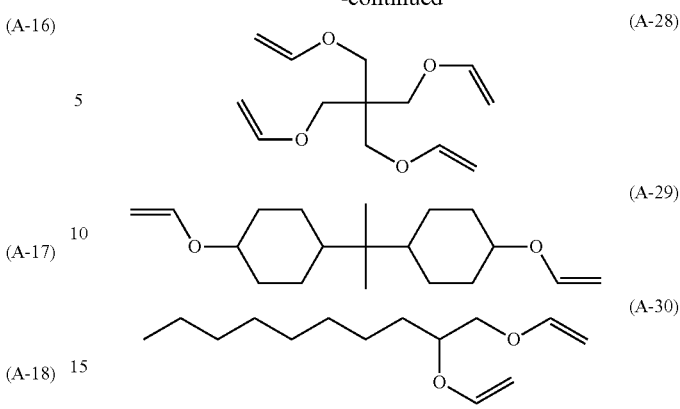

(A-28)
(A-29)
(A-30)

The following, for example, are preferred among the preceding: dodecyl vinyl ether (A-3), dicyclopentadiene vinyl ether (A-8), cyclohexanedimethanol divinyl ether (A-17), tricyclodecane vinyl ether (A-10), dipropylene glycol divinyl ether (A-19), trimethylolpropane trivinyl ether (A-24), 2-ethyl-1,3-hexanediol divinyl ether (A-25), 2,4-diethyl-1,5-pentanediol divinyl ether (A-26), 2-butyl-2-ethyl-1,3-propanediol divinyl ether (A-27), neopentyl glycol divinyl ether (A-23), pentaerythritol tetravinyl ether (A-28), and 1,2-decanediol divinyl ether (A-30).

<Polymerization Initiator>

A reaction referred to as an initiation reaction is required in order to start the polymerization reaction of the liquid polymerizable compound. The substance used for this is a polymerization initiator.

In the present invention, when the liquid polymerizable compound is a component that can undergo polymerization through a photopolymerization reaction, a photopolymerization initiator, which reacts to light at a prescribed wavelength and thereby generates an acid or a radical, may be used, and examples thereof are given in the following.

Cationic photopolymerization initiators can be exemplified by diazonium salts in which the counterion is an anion such as a halogen-type anion, a sulfonic acid-type anion, a carboxylic acid-type anion, or a sulfate anion; onium salt compounds such as a sulfonium salt, iodonium salt, and phosphonium salt; sulfone compounds; sulfonate ester compounds; sulfonimide compounds; and diazomethane compounds, but are not limited to the preceding. Radical photopolymerization initiators can be exemplified by benzoin derivatives, but are not limited thereto.

In addition, when a cationic photopolymerization initiator is used, the use of a photopolymerization initiator as given by the following formula (4) is preferred in the present invention because this provides little reduction in the volume resistivity of the liquid polymerizable compound.

formula (4)

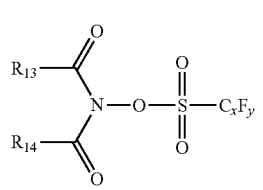

[In formula (4), $R_{13}$ and $R_{14}$ are bonded to each other to form a ring structure; x represents an integer from 1 to 8; and y represents an integer from 3 to 17.]

The ring structure formed by the bonding of $R_{13}$ with $R_{14}$ can be exemplified by 5-membered rings and 6-membered rings. Specific examples of the ring structure formed by the bonding of $R_{13}$ with $R_{14}$ are succinimide structures, phthalimide structures, norbornene dicarboximide structures, naphthalene dicarboximide structures, cyclohexane dicarboximide structures, and epoxycyclohexene dicarboximide structures.

These ring structures may also have, for example, the following as substituents: an alkyl group, alkyloxy group, alkylthio group, aryl group, aryloxy group, or arylthio group.

The $C_xF_y$ in general formula (4) can be exemplified by linear-chain alkyl groups in which the hydrogen atom has been substituted by the fluorine atom (RF1), branched-chain alkyl groups in which the hydrogen atom has been substituted by the fluorine atom (RF2), cycloalkyl groups in which the hydrogen atom has been substituted by the fluorine atom (RF3), and aryl groups in which the hydrogen atom has been substituted by the fluorine atom (RF4).

The linear-chain alkyl groups in which the hydrogen atom has been substituted by the fluorine atom (RF1) can be exemplified by the trifluoromethyl group (x=1, y=3), pentafluoroethyl group (x=2, y=5), heptafluoro-n-propyl group (x=3, y=7), nonafluoro-n-butyl group (x=4, y=9), perfluoro-n-hexyl group (x=6, y=13), and perfluoro-n-octyl group (x=8, y=17).

The branched-chain alkyl groups in which the hydrogen atom has been substituted by the fluorine atom (RF2) can be exemplified by the perfluoroisopropyl group (x=3, y=7), perfluoro-tert-butyl group (x=4, y=9), and perfluoro-2-ethylhexyl group (x=8, y=17).

The cycloalkyl groups in which the hydrogen atom has been substituted by the fluorine atom (RF3) can be exemplified by the perfluorocyclobutyl group (x=4, y=7), perfluorocyclopentyl group (x=5, y=9), perfluorocyclohexyl group (x=6, y=11), and perfluoro(1-cyclohexyl)methyl group (x=7, y=13).

The aryl groups in which the hydrogen atom has been substituted by the fluorine atom (RF4) can be exemplified by the pentafluorophenyl group (x=6, y=5) and 3-trifluoromethyltetrafluorophenyl group (x=7, y=7).

For the $C_xF_y$ in general formula (4), the linear-chain alkyl groups (RF1), branched-chain alkyl groups (RF2), and aryl groups (RF4) are preferred from the standpoint of the ease of acquisition and the decomposability of the sulfonate ester moiety. The linear-chain alkyl groups (RF1) and aryl groups (RF4) are more preferred. The trifluoromethyl group (x=1, y=3), pentafluoroethyl group (x=2, y=5), heptafluoro-n-propyl group (x=3, y=7), nonafluoro-n-butyl group (x=4, y=9), and pentafluorophenyl group (x=6, y=5) are particularly preferred.

A single polymerization initiator can be used by itself or two or more can be used in combination.

The content of the polymerization initiator is not particularly limited, but, expressed per 100 mass parts of the liquid polymerizable compound, is preferably at least 0.01 mass parts and not more than 5 mass parts, more preferably at least 0.05 mass parts and not more than 1 mass part, and even more preferably at least 0.1 mass parts and not more than 0.5 mass parts.

Specific examples (example compounds B-1 to B-27) of the photopolymerization initiator with formula (4) are given below, but the present invention is not limited to or by these examples.

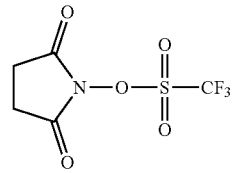

(B-1)

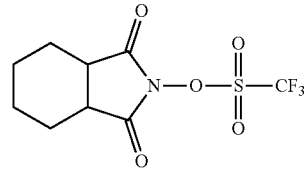

(B-2)

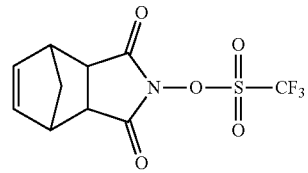

(B-3)

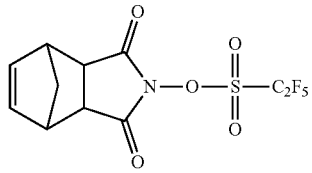

(B-4)

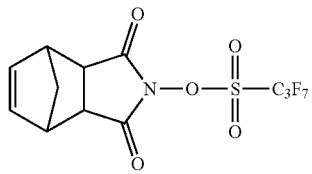

(B-5)

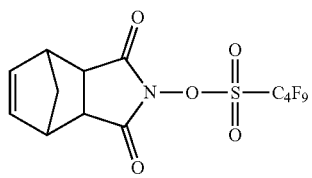

(B-6)

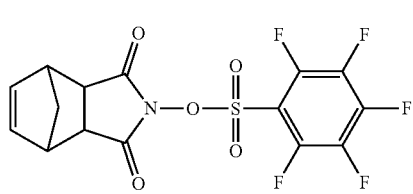

(B-7)

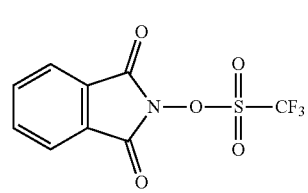

(B-8)

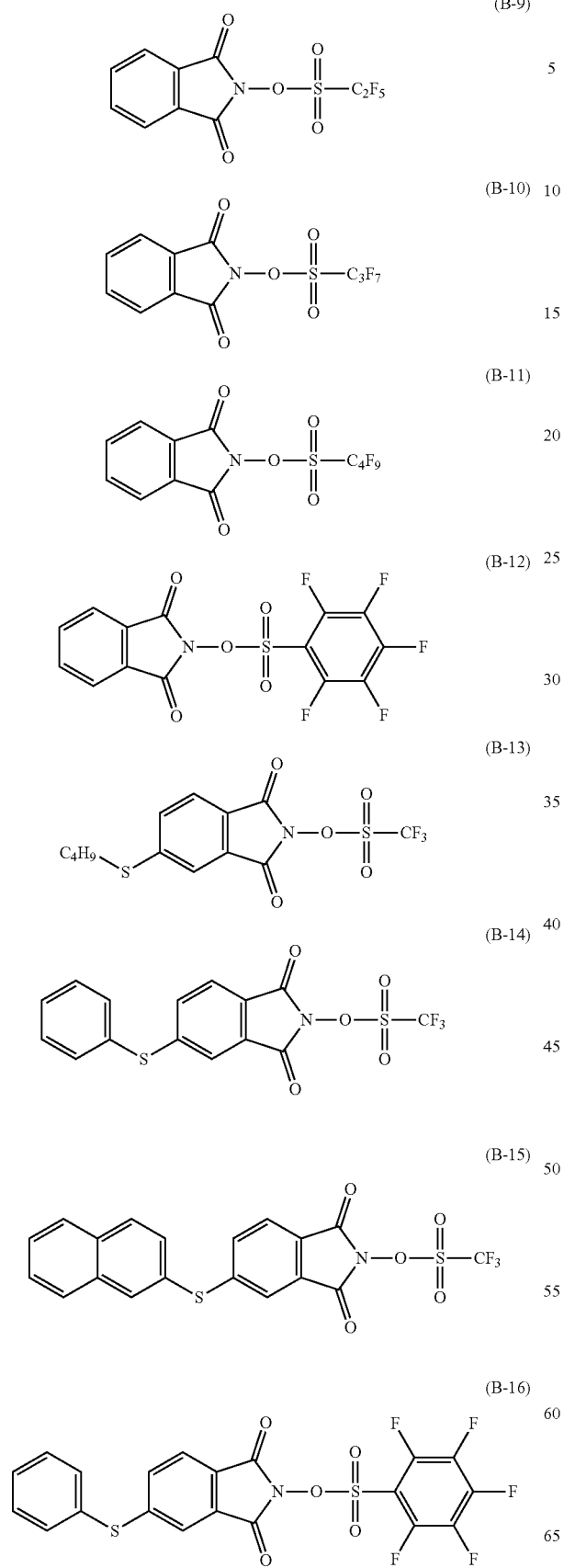
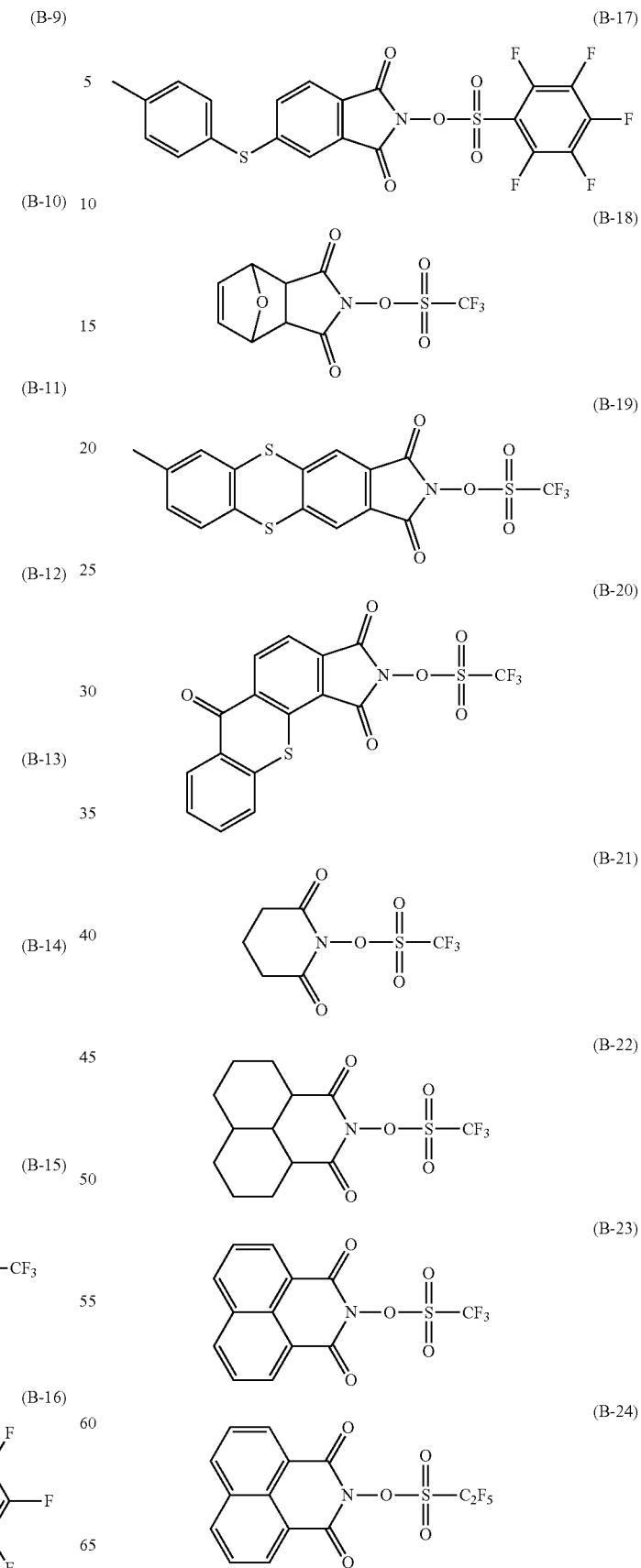

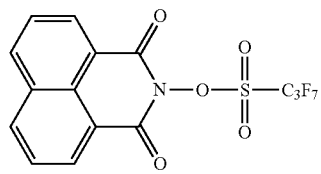
(B-25)

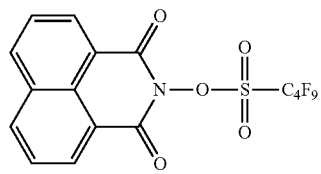
(B-26)

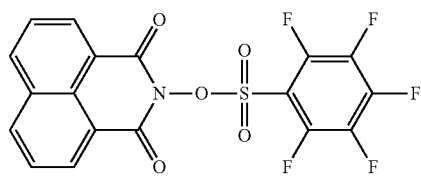
(B-27)

<Sensitizer>

As necessary, a sensitizer may be present in the liquid developer of the present invention with the goals of, for example, improving the acid-generating efficiency of the photopolymerization initiator and extending the photosensitive wavelengths to longer wavelengths.

The sensitizer should be able to sensitize the photopolymerization initiator through an electron transfer mechanism or energy transfer mechanism, but is not otherwise particularly limited.

Specific examples are aromatic polycondensed ring compounds such as anthracene, 9,10-dialkoxyanthracene, pyrene, and perylene; aromatic ketone compounds such as acetophenone, benzophenone, thioxanthone, and Michler's ketone; and heterocyclic compounds such as phenothiazine and N-aryloxazolidinone.

The content of the sensitizer is selected as appropriate in correspondence to the goal, and generally is 0.1 to 10 mass parts and preferably 1 to 5 mass parts per 1 mass part of the photopolymerization initiator.

A co-sensitizer may also be added to the liquid developer of the present invention with the goal of improving the electron transfer efficiency or energy transfer efficiency between the aforementioned sensitizer and the photopolymerization initiator.

Specific examples are naphthalene compounds such as 1,4-dihydroxynaphthalene, 1,4-dimethoxynaphthalene, 1,4-diethoxynaphthalene, 4-methoxy-1-naphthol, and 4-ethoxy-1-naphthol, and benzene compounds such as 1,4-dihydroxybenzene, 1,4-dimethoxybenzene, 1,4-diethoxybenzene, 1-methoxy-4-phenol, and 1-ethoxy-4-phenol.

The content of the co-sensitizer is selected as appropriate in correspondence to the goal, but is generally 0.1 to 10 mass parts and preferably 0.5 to 5 mass parts per 1 mass part of the sensitizer.

<Cationic Polymerization Inhibitor>

A cationic polymerization inhibitor can also be incorporated in the liquid developer of the present invention.

The cationic polymerization inhibitor can be exemplified by alkali metal compounds and/or alkaline-earth metal compounds and by amines.

The amines can be exemplified by alkanolamines, N,N-dimethylalkylamines, N,N-dimethylalkenylamines, and N,N-dimethylalkynylamines.

Specific examples are triethanolamine, triisopropanolamine, tributanolamine, N-ethyldiethanolamine, propanolamine, n-butylamine, sec-butylamine, 2-aminoethanol, 2-methylaminoethanol, 3-methylamino-1-propanol, 3-methylamino-1,2-propanediol, 2-ethylaminoethanol, 4-ethylamino-1-butanol, 4-(n-butylamino)-1-butanol, 2-(t-butylamino)ethanol, N,N-dimethylundecanolamine, N,N-dimethyldodecanolamine, N,N-dimethyltridecanolamine, N,N-dimethyltetradecanolamine, N,N-dimethylpentadecanolamine, N,N-dimethylnonadecylamine, N,N-dimethylicosylamine, N,N-dimethyleicosylamine, N,N-dimethylheneicosylamine, N,N-dimethyldocosylamine, N,N-dimethyltricosylamine, N,N-dimethyltetracosylamine, N,N-dimethylpentacosylamine, N,N-dimethylpentanolamine, N,N-dimethylhexanolamine, N,N-dimethylheptanolamine, N,N-dimethyloctanolamine, N,N-dimethylnonanolamine, N,N-dimethyldecanolamine, N,N-dimethylnonylamine, N,N-dimethyldecylamine, N,N-dimethylundecylamine, N,N-dimethyldodecylamine, N,N-dimethyltridecylamine, N,N-dimethyltetradecylamine, N,N-dimethylpentadecylamine, N,N-dimethylhexadecylamine, N,N-dimethylheptadecylamine, and N,N-dimethyloctadecylamine. In addition to these, for example, a quaternary ammonium salt may also be used. The cationic polymerization inhibitor is particularly preferably a secondary amine.

The content of the cationic polymerization inhibitor is preferably 1 to 5,000 ppm on a mass basis in the liquid developer.

<Radical Polymerization Inhibitor>

The liquid developer of the present invention may contain a radical polymerization inhibitor.

For example, in the case of a liquid developer that contains a vinyl ether compound, during storage the photopolymerization initiator may undergo a very slight decomposition and thereby convert into a radical compound and a polymerization caused by this radical compound may then be induced. A radical polymerization inhibitor may be added to prevent this.

Usable radical polymerization inhibitors can be exemplified by phenolic hydroxy group-containing compounds; quinones such as methoquinone (hydroquinone monomethyl ether), hydroquinone, and 4-methoxy-1-naphthol; hindered amine antioxidants; 1,1-diphenyl-2-picrylhydrazyl free radical; N-oxyl free radical compounds; nitrogen-containing heterocyclic mercapto compounds; thioether antioxidants; hindered phenol antioxidants; ascorbic acids; zinc sulfate; thiocyanates; thiourea derivatives; saccharides; phosphoric acid-type antioxidants; nitrites; sulfites; thiosulfates; hydroxylamine derivatives; aromatic amines; phenylenediamines; imines; sulfonamides; urea derivatives; oximes; polycondensates of dicyandiamide and polyalkylenepolyamine; sulfur-containing compounds such as phenothiazine; complexing agents based on tetraazaannulene (TAA); and hindered amines.

Phenolic hydroxy group-containing compounds, N-oxyl free radical compounds, 1,1-diphenyl-2-picrylhydrazyl free radical, phenothiazine, quinones, and hindered amines are preferred from the standpoint of preventing the liquid developer from undergoing a viscosity increase. N-oxyl free radical compounds are more preferred.

The content of the radical polymerization inhibitor is preferably 1 to 5,000 ppm on a mass basis in the liquid developer.

<Charge Control Agent>

The carrier liquid may contain, in combination with the aforementioned compound 1, an additional charge control agent with the goal of modifying the charging performance of the toner particle.

A known charge control agent can be used as this additional charge control agent within a range at which the volume resistivity for the liquid developer does not undergo an excessive decline and the viscosity does not undergo an excessive increase.

Examples of specific compounds are as follows: fats and oils such as linseed oil and soy oil; alkyd resins; halogen polymers; aromatic polycarboxylic acids; acidic group-containing water-soluble dyes; oxidative condensates of aromatic polyamines; metal soaps such as zirconium naphthenate, cobalt naphthenate, nickel naphthenate, iron naphthenate, zinc naphthenate, cobalt octoate, nickel octoate, zinc octoate, cobalt dodecanoate, nickel dodecanoate, zinc dodecanoate, aluminum stearate, aluminum tristearate, and cobalt 2-ethylhexanoate; metal sulfonates such as petroleum-based metal sulfonates and metal salts of sulfosuccinate esters; phospholipids such as lecithin; metal complexes of salicylic acid and benzilic acid, e.g., aluminum 3,5-di-tert-butylsalicylate and borobis(1,1-diphenyl-1-oxoacetyl) potassium salt (LR-147 (product name), from Japan Carlit Co., Ltd.); polyvinylpyrrolidone resins; polyamide resins; sulfonic acid-containing resins; and hydroxybenzoic acid derivatives.

The content of this additional charge control agent is not particularly limited, but, expressed per 100 mass parts of the toner particle, is preferably at least 0.01 mass parts and not more than 10.00 mass parts and more preferably at least 0.05 mass parts and not more than 5.00 mass parts. It is even more preferably at least 0.10 mass parts and not more than 3.00 mass parts and is particularly preferably at least 0.30 mass parts and not more than 2.00 mass parts.

<The Toner Particle>

The toner particle contains a binder resin and a colorant as constituent components.

(Binder Resin)

A known binder resin can be used—as long as it is insoluble in the carrier liquid and exhibits a fixing performance for the adherend, e.g., paper or plastic film—as the binder resin present in the toner particle.

Here, this "insoluble in the carrier liquid" is provided as an indicator that not more than 1 mass part of the binder resin dissolves at a temperature of 25° C. in 100 mass parts of the carrier liquid.

Specific examples of this binder resin are resins such as epoxy resins, polyester resins, (meth)acrylic resins, styrene-(meth)acrylic resins, alkyd resins, polyethylene resins, ethylene-(meth)acrylic resins, and rosin-modified resins. As necessary, a single one of these may be used or two or more may be used in combination.

There are no particular limitations on the content of the binder resin, but it is preferably 50 to 1,000 mass parts per 100 mass parts of the colorant.

<Colorant>

There are no particular limitations on the colorant incorporated in the toner particle, and, for example, any generally commercially available organic pigment, organic dye, inorganic pigment, or pigment dispersed in, e.g., an insoluble resin as a dispersion medium, can be used, or a pigment having a resin grafted to its surface can be used.

These pigments can be exemplified by the pigments described in, for example, "Industrial Organic Pigments", W. Herbst and K. Hunger.

The following are specific examples of pigments that present a yellow color:

C. I. Pigment Yellow 1, 2, 3, 4, 5, 6, 7, 10, 11, 12, 13, 14, 15, 16, 17, 23, 62, 65, 73, 74, 83, 93, 94, 95, 97, 109, 110, 111, 120, 127, 128, 129, 147, 151, 154, 155, 168, 174, 175, 176, 180, 181, and 185, and C. I. Vat Yellow 1, 3, and 20.

Pigments that present a red or magenta color can be exemplified by the following:

C. I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48:2, 48:3, 48:4, 49, 50, 51, 52, 53, 54, 55, 57:1, 58, 60, 63, 64, 68, 81:1, 83, 87, 88, 89, 90, 112, 114, 122, 123, 146, 147, 150, 163, 184, 202, 206, 207, 209, 238, and 269; C. I. Pigment Violet 19; and C. I. Vat Red 1, 2, 10, 13, 15, 23, 29, and 35.

Pigments that present a blue or cyan color can be exemplified by the following:

C. I. Pigment Blue 2, 3, 15:2, 15:3, 15:4, 16, and 17; C. I. Vat Blue 6; C. I. Acid Blue 45; and copper phthalocyanine pigments in which the phthalocyanine skeleton is substituted by 1 to 5 phthalimidomethyl groups.

Pigments that present a green color can be exemplified by the following:

C. I. Pigment Green 7, 8, and 36.

Pigments that present an orange color can be exemplified by the following:

C. I. Pigment Orange 66 and 51.

Pigments that present a black color can be exemplified by the following:

carbon black, titanium black, and aniline black.

Pigments that present a white color can be exemplified by the following:

basic lead carbonate, zinc oxide, titanium oxide, and strontium titanate.

A dispersing means adapted to the toner particle production method may be used to disperse the pigment in the toner particle. Devices that can be used as this dispersing means are, for example, a ball mill, sand mill, attritor, roll mill, jet mill, homogenizer, paint shaker, kneader, agitator, Henschel mixer, colloid mill, ultrasonic homogenizer, pearl mill, wet jet mill, and so forth.

A pigment dispersing agent may also be added when pigment dispersion is carried out. The pigment dispersing agent can be exemplified by hydroxyl group-bearing carboxylate esters, the salts of long-chain polyaminoamides and high molecular weight acid esters, the salts of high molecular weight polycarboxylic acids, high molecular weight unsaturated acid esters, high molecular weight copolymers, modified polyacrylates, aliphatic polybasic carboxylic acids, naphthalenesulfonic acid/formalin condensates, polyoxyethylene alkyl phosphate esters, and pigment derivatives. The use of commercially available high molecular weight pigment dispersing agents such as the Solsperse series from The Lubrizol Corporation is also preferred.

A synergist adapted to the particular pigment may also be used as a pigment dispersing aid.

These pigment dispersing agents and pigment dispersing aids are added preferably at 1 to 50 mass parts per 100 mass parts of the pigment.

<Charge Adjuvant>

A charge adjuvant can be incorporated in the toner particle with the goal of adjusting the charging performance of the toner particle. A known charge adjuvant can be used.

Examples of specific compounds are as follows: metal soaps such as zirconium naphthenate, cobalt naphthenate, nickel naphthenate, iron naphthenate, zinc naphthenate, cobalt octoate, nickel octoate, zinc octoate, cobalt dodecanoate, nickel dodecanoate, zinc dodecanoate, aluminum stearate, aluminum tristearate, and cobalt 2-ethylhexanoate; metal sulfonates such as petroleum-based metal sulfonates and the metal salts of sulfosuccinate esters; phospholipids such as lecithin; metal salicylates such as metal t-butylsalicylate complexes; polyvinylpyrrolidone resins; polyamide resins; sulfonic acid-containing resins; and hydroxybenzoic acid derivatives.

[Other Additives]

In addition to those described above, various known additives may as necessary be used in the liquid developer of the present invention to respond to the goals of improving the compatibility with recording media, improving the storage stability, improving the image storability, and improving other characteristics. For example, the following can be selected as appropriate and used: surfactant, lubricant, filler, antifoaming agent, ultraviolet absorber, antioxidant, antifading agent, fungicide, anticorrosion agent, and so forth.

In the present invention, the method of producing the liquid developer is not particularly limited, and it can be exemplified by known methods, for example, the coacervation method and wet pulverization method.

An example of a general production method is a production method in which a colorant, e.g., a pigment, a binder resin, other additives, and a dispersion medium, e.g., a carrier liquid, are mixed; pulverization is carried out using, e.g., a bead mill, to obtain a dispersion of toner particles; and the obtained toner particle dispersion, additives, carrier liquid, and so forth are mixed to obtain the liquid developer.

In the present invention, the toner particle dispersion is obtained by mixing the colorant, binder resin, other additives, and carrier liquid and carrying out pulverization using, for example, a bead mill. The liquid developer can be obtained by mixing the obtained toner particle dispersion, the aforementioned compound 1 dispersed in carrier liquid, the carrier liquid, and so forth.

Here, shear force is preferably applied and/or a heat treatment is preferably applied to the mixture obtained by mixing the toner particle dispersion, the compound 1 dispersed in carrier liquid, the carrier liquid, and so forth.

A known stirrer, emulsifying apparatus, or disperser may be used to apply the shear force.

Examples here are ultrasonic dispersers, jet mills, pressure-type homogenizers, colloid mills, ball mills, sand mills, paint shakers, and so forth.

There are no limitations on the ultrasonic disperser, and it can be exemplified by the UH-600S ultrasonic disperser (SMT Corporation).

The heat treatment, on the other hand, can be done, for example, at at least 50° C. and not more than 70° C.

When the application of shear force and the heat treatment are both carried out, their sequence is not particularly limited, but the heat treatment is preferably carried out after the application of shear force.

Through the application of shear force and/or the application of a heat treatment to the aforementioned mixture, the coarse particles of compound 1 are reduced and an excellent dispersion stability can be imparted to the toner particle.

The details of the aforementioned coacervation method are described in, for example, Japanese Patent Application Laid-open No. 2003-241439, WO 2007/000974, and WO 2007/000975.

In the coacervation method, a pigment, resin, solvent that dissolves the resin, and solvent that does not dissolve the resin are mixed and the solvent that dissolves the resin is then removed from the mixture to cause the resin that had been dissolved to precipitate, thereby creating a dispersion of pigment-enclosing toner particles in the solvent that does not dissolve the resin.

The details of the wet pulverization method, on the other hand, are described in, for example, WO 2006/126566 and WO 2007/108485.

In the wet pulverization method, the pigment and binder resin are kneaded at or above the melting point of the binder resin; this is followed by a dry pulverization; and the obtained pulverized material is subjected to a wet pulverization in an electrically insulating medium, thereby creating a dispersion of toner particles in the electrically insulating medium.

Known methods such as these can be used in the present invention.

Viewed from the perspective of obtaining a high-definition image, the volume-average particle diameter of the toner particle is preferably at least 0.05 μm and not more than 5 μm and is more preferably at least 0.05 μm and not more than 1 μm.

In the present invention, the toner particle concentration used in the liquid developer can be freely adjusted in conformity with the image-forming apparatus that is used, but is desirably made approximately at least 1 mass % and not more than 70 mass %.

<Characteristics of the Liquid Developer>

The liquid developer of the present invention is preferably used having been prepared to have the following property values. Thus, viewed from the perspective of obtaining a suitable toner particle electrophoretic mobility, the viscosity of the developer at 25° C. for a toner particle concentration of 2 mass % is preferably at least 0.5 mPa·s and not more than 100 mPa·s.

In addition, viewed from the perspective of not causing a drop in the potential of the electrostatic latent image, the volume resistivity of the liquid developer is preferably at least $1 \times 10^9$ Ω·cm and not more than $1 \times 10^{13}$ Ω·cm and is more preferably at least $1 \times 10^{10}$ Ω·cm and not more than $1 \times 10^{13}$ Ω·cm.

<The Image-forming Apparatus>

The liquid developer of the present invention can be advantageously used in common image-forming apparatuses that utilize an electrophotographic system.

<Light Source>

When a curable form of the liquid developer of the present invention is used, the image is fixed by curing by the application of energy immediately after transfer to the recording medium.

There are no particular limitations on the energy source used by the present invention, but ultraviolet radiation is advantageously used.

The light source here for carrying out ultraviolet irradiation is suitably, for example, a mercury lamp, metal halide lamp, excimer laser, ultraviolet laser, cold cathode tube, hot cathode tube, black light, or light-emitting diode (LED). A strip-shaped metal halide lamp, cold cathode tube, hot cathode tube, mercury lamp, black light, or LED is preferred.

The ultraviolet exposure dose is preferably from 0.1 to 1,000 mJ/cm$^2$.

The measurement methods used in the present invention are given in the following.

<Method for Measuring the Molecular Weight>

The molecular weight of the binder resins and so forth is determined as polystyrene using gel permeation chromatography (GPC). The measurement of the molecular weight by GPC is carried out as follows.

A solution is prepared by adding the sample to the eluent indicated below to provide a sample concentration of 1.0 mass % and dissolving by standing for 24 hours at room temperature. This solution is filtered across a solvent-resistant membrane filter with a pore diameter of 0.20 µm to obtain the sample solution, and measurement is performed under the following conditions.

instrument: "HLC-8220GPC" high-performance GPC instrument (from the Tosoh Corporation)
column: 2×LF-804
eluent: tetrahydrofuran (THF)
flow rate: 1.0 mL/min
oven temperature: 40° C.
sample injection amount: 0.025 mL The molecular weight calibration curve used to determine the molecular weight of the sample was constructed using polystyrene resin standards [TSK Standard Polystyrene F-850, F-450, F-288, F-128, F-80, F-40, F-20, F-10, F-4, F-2, F-1, A-5000, A-2500, A-1000, and A-500, from the Tosoh Corporation].

<Compositional Analysis>

The following procedure is used for the structural determination of, inter alia, the compounds.

The $^1$H-NMR and $^{13}$C-NMR spectra are measured using an ECA-400 (400 MHz) from JEOL Ltd.

The measurements were carried out at 25° C. in a deuterated solvent containing tetramethylsilane as the internal standard. The chemical shift values are given as the shift value (δ value) in ppm assigning 0 to the tetramethylsilane internal standard.

EXAMPLES

The present invention is more specifically described through the examples provided below, but the present invention is not limited to or by these.

Unless specifically indicated otherwise, "parts" and "%" denote, respectively, "mass parts" and "mass %" in the following description.

Example 1

(Toner Particle Production)

25 parts of NUCREL N1525 (ethylene-methacrylic acid resin, Du Pont-Mitsui Polychemicals Co., Ltd.) and 75 parts of dodecyl vinyl ether (example compound A-3) as a liquid cationically polymerizable compound were introduced into a separable flask and the temperature was raised over 1 hour to 130° C. on an oil bath while stirring at 200 rpm with a Three-One motor. After holding for 1 hour at 130° C., gradual cooling was carried out at a ramp down rate of 15° C. per 1 hour to produce a binder resin dispersion. The obtained binder resin dispersion was a white paste.

59.40 parts of this binder resin dispersion, Pigment Blue 15:3 (4.95 parts) as the pigment, 0.20 parts of aluminum tristearate as a charge adjuvant, and 35.45 parts of dodecyl vinyl ether were filled into a planetary bead mill (Classic Line P-6, Fritsch) along with zirconia beads having a diameter of 0.5 mm, and pulverization was carried out at 200 rpm for 4 hours at room temperature to obtain a toner particle dispersion (solids fraction=20 mass %).

The toner particles contained in the obtained toner particle dispersion had a volume-average particle diameter of 0.85 µm (measured with a NANOTRAC 150 from Nikkiso Co., Ltd., a particle size distribution analyzer based on dynamic light scattering (DLS)).

(Preparation of the Liquid Developer)

2.0 parts of hydrogenated lecithin (LECINOL S-10EX, Nikko Chemicals Co., Ltd.) as the compound with formula (1) and 98.0 parts of dodecyl vinyl ether were introduced into a separable flask, and a dispersion of the hydrogenated lecithin was prepared by stirring at 200 rpm using a Three-One motor. The obtained dispersion of hydrogenated lecithin was a white suspension.

79.42 parts of the aforementioned toner particle dispersion, 11.91 parts of the aforementioned dispersion of hydrogenated lecithin, 8.36 parts of cyclohexanedimethanol divinyl ether (example compound A-17) as a liquid cationically polymerizable compound, 0.08 parts of LIPIDURE (registered trademark)-S (NOF Corporation) as a polymer compound 3, and example compound B-3 (0.23 parts) as a photopolymerization initiator were mixed, and the obtained mixture was subjected to the application of shear force for 30 minutes using a UH-600S ultrasonic disperser (SMT Corporation) at a duty ratio of 33%, followed by a heat treatment for 4 hours at 70° C. on a water bath to obtain a liquid developer.

<Property Evaluations>

(Evaluation of the Electrophoretic Mobility)

The electrophoretic mobility of the obtained liquid developer was measured using the following procedure and was evaluated according to the evaluation criteria given below.

A sample prepared by dilution with carrier liquid (the liquid cationically polymerizable compound used) so as to provide a toner particle concentration of 1 mass %, was held by capillary force between parallel flat-plate electrodes consisting of metal electrodes with a thickness of 300 µm and a width of 20 mm facing each other across a gap of 100 µm.

The status of electrophoresis when a potential difference of 100 V (field strength=1×10$^6$ V/m) was applied across the parallel flat-plate electrodes was photographed with a high-speed camera (FASTCAM SA-1, Photron Limited) connected to an optical microscope.

The obtained image was imported into ImageJ image processing software (developer: Wayne Rasband (NIH)), and the average electrophoretic mobility of the particles was calculated by the particle image velocimetry method (PIV method). The electrophoretic mobility of the particles was taken to be negative in the case of migration to the anode and positive in the case of migration to the cathode. The evaluation of the electrophoretic mobility was scored using the following criteria.

(Evaluation Criteria)

10: the average electrophoretic mobility is at least 1×10$^{-9}$ m$^2$/V·s

9: the average electrophoretic mobility is at least 8×10$^{-10}$ m$^2$/V·s and less than 1×10$^{-9}$ m$^2$/V·s 8: the average electrophoretic mobility is at least 7×10$^{-10}$ m$^2$/V·s and less than 8×10$^{-10}$ m$^2$/V·s 7: the average electrophoretic mobility is at least 6×10$^{-10}$ m$^2$/V·s and less than 7×10$^{-10}$ m$^2$/V·s 6: the average electrophoretic mobility is at least 5×10$^{-10}$ m$^2$/V·s and less than 6×10$^{-10}$ m$^2$/V·s 5: the average electrophoretic mobility is at least 4×10$^{-10}$ m$^2$/V·s and less than 5×10$^{-10}$ m$^2$/V·s 4: the average electrophoretic mobility is at least 3×10$^{-10}$ m$^2$/V·s and less than 4×10$^{-10}$ m$^2$/V·s 3: the average electrophoretic mobility is at least 2×10$^{-10}$ m$^2$/V·s and less than 3×10$^{-10}$ m$^2$/V·s 2: the average electrophoretic mobility is at least 1×10$^{-10}$ m$^2$/V·s and less than 2×10$^{-10}$ m$^2$/V·s 1: the average electrophoretic mobility is less than 1×10$^{-10}$ m$^2$/V·s The effects of the present invention with regard to electrophoretic mobility and amount of charge were considered to be operative when the average electrophoretic mobility was at least $5 \times 10^{-10}$ m$^2$/V·s.

(Evaluation of the Volume Resistivity)

The volume resistivity of the liquid developer was measured using an R8340A digital ultrahigh resistance/microcurrent meter (Advantest Corporation). For the measurement, 25 mL of the liquid developer was introduced into an SME-8330 liquid sample electrode (Hioki E.E. Corporation) and the measurement was carried out by the application of 1,000 V direct current at a room temperature of 25° C.

The evaluation of the volume resistivity was scored using the following evaluation criteria. (Evaluation criteria)
10: the volume resistivity is at least $3 \times 10^{11}$ Ω·cm
9: the volume resistivity is at least $1 \times 10^{11}$ Ω·cm and less than $3 \times 10^{11}$ Ω·cm
8: the volume resistivity is at least $7 \times 10^{10}$ Ω·cm and less than $1 \times 10^{11}$ Ω·cm
7: the volume resistivity is at least $5 \times 10^{10}$ Ω·cm and less than $7 \times 10^{10}$ Ω·cm
6: the volume resistivity is at least $3 \times 10^{10}$ Ω·cm and less than $5 \times 10^{10}$ Ω·cm
5: the volume resistivity is at least $1 \times 10^{10}$ Ω·cm and less than $3 \times 10^{10}$ Ω·cm
4: the volume resistivity is at least $7 \times 10^{9}$ Ω·cm and less than $1 \times 10^{10}$ Ω·cm
3: the volume resistivity is at least $5 \times 10^{9}$ Ω·cm and less than $7 \times 10^{9}$ Ω·cm
2: the volume resistivity is at least $3 \times 10^{9}$ Ω·cm and less than $5 \times 10^{9}$ Ω·cm
1: the volume resistivity is less than $3 \times 10^{9}$ Ω·cm The effects of the present invention with regard to volume resistivity were considered to be operative when the volume resistivity was at least $1 \times 10^{10}$ Ω·cm.

(Evaluation of the Developing Performance)

An electrostatic pattern was formed at a surface charge of 500 V on electrostatic recording paper, and development was performed using the liquid developer at a process speed of 20 mm/sec using a roller developing device that used a metal roller. The gap between the roller and the electrostatic recording paper (the development gap) was set to 34 μm. The quality of the obtained image was visually inspected.

The evaluation of the developing performance was scored using the following criteria.
10: the obtained image had a very high density and a very high definition
9: the obtained image had a very high density and a high definition
8: the obtained image had a high density and a high definition
7: a slight image density non-uniformity is present, or slight image blurring is seen
6: image density non-uniformity is seen in spots, but a generally good development is recognized
5: image density non-uniformity or image blurring is seen in spots, but a generally good development is recognized
4: image blurring was produced and development was unsatisfactory
3: image density non-uniformity and/or image blurring was produced and development was unsatisfactory
2: severe image density non-uniformity and/or image blurring was produced and development was unsatisfactory
1: development could not be carried out The effects of the present invention with regard to developing performance were considered to be operative at a rank of 5 or larger.

(Evaluation of the Redispersibility)

The liquid developer was concentrated with a centrifugal separator followed by dilution with the carrier liquid (the liquid cationically polymerizable compound used) to provide a toner particle concentration of 15 mass %, and redispersion was then carried out using a UH-600S ultrasonic disperser (SMT Corporation).

The particle diameter of the toner particles in the liquid developer was measured before and after concentration; the measurement was carried out as the volume-average particle diameter using a NANOTRAC 150 (Nikkiso Co., Ltd.), a particle size distribution analyzer based on dynamic light scattering (DLS), at a range setting of 0.001 μm to 10 μm.

The redispersibility of the toner particles in the liquid developer was evaluated as the ratio of the toner particle diameter post-versus-pre-concentration (toner particle diameter post-concentration/toner particle diameter pre-concentration).

The evaluation of the redispersibility was scored using the following criteria.
10: (ratio of the toner particle diameter post-versus-pre-concentration)≤1.1
9: 1.1<(ratio of the toner particle diameter post-versus-pre-concentration)≤1.2
8: 1.2<(ratio of the toner particle diameter post-versus-pre-concentration)≤1.3
7: 1.3<(ratio of the toner particle diameter post-versus-pre-concentration)≤1.4
6: 1.4<(ratio of the toner particle diameter post-versus-pre-concentration)≤1.5
5: 1.5<(ratio of the toner particle diameter post-versus-pre-concentration)≤1.6
4: 1.6<(ratio of the toner particle diameter post-versus-pre-concentration)≤1.7
3: 1.7<(ratio of the toner particle diameter post-versus-pre-concentration)≤1.8
2: 1.8<(ratio of the toner particle diameter post-versus-pre-concentration)≤2.0
1: 2.0<(ratio of the toner particle diameter post-versus-pre-concentration)

The effects of the present invention with regard to redispersibility were considered to be operative at a rank of 7 or larger.

(Evaluation of the Ultraviolet Fixing Performance)

The liquid developer was bar coated (a film with a thickness of 13.7 μm was formed) at 25° C. using a wire bar (No. 6) [supplier: Matsuo Sangyo Co., Ltd.] on a polyethylene terephthalate film, and a cured film was formed by exposure to a dose of 120 mJ/cm$^2$ (measurement wavelength=365 nm) from a high-pressure mercury lamp having a lamp output of 120 mW/cm$^2$. Immediately after curing, the presence/absence of surface tack (stickiness) was checked by finger contact with the film surface.

The evaluation of the ultraviolet fixing performance was scored using the following criteria.
10: Tack was not detected at all and the fixing performance was very good.
9: While a very slight tack was detected, the fixing performance was good.
8: While tack was detected in a small area, the fixing performance was substantially good.
7: While tack was detected in some areas, the fixing performance was generally good.
6: Tack is detected and the fixing performance cannot be regarded as satisfactory.
5: Tack is detected over a large area and the fixing performance was unsatisfactory.

4: Tack is detected over the entire area.
3: An uncured area is detected.
2: The film is slightly detached during finger contact, or curing has not occurred in part.
1: The film is detached during finger contact, or curing is entirely absent.

The effects of the present invention with regard to the ultraviolet fixing performance were considered to be operative at a rank of 7 or larger.

Examples 2 to 14 and 20 and Comparative Examples 1 to 6

Liquid developers were obtained proceeding as in Example 1, but using the blends described in Table 1 for the compound with formula (1), the carrier liquid, and the polymer compound or charge control agent of Example 1 and using the application of shear force and the heat treatment as described in Table 1.

Examples 15 to 19 and Comparative Examples 7 to 12

Liquid developers were obtained proceeding as in Example 1 with the following exceptions: MORESCO White MT-30P (Moresco Corporation) was used in place of the dodecyl vinyl ether and cyclohexanedimethanol divinyl ether of Example 1; the compound with formula (1) and the polymer compound or charge control agent were blended as described in Table 2; and the application of shear force and the heat treatment were as described in Table 2.

In Example 7, the polymer compound a described below, which was a polymer compound having a structural unit with formula (2) (polymer compound 2), was used in place of the LIPIDURE (registered trademark)-S (polymer compound 3).

<Synthesis of Polymer Compound A>

136.4 parts of 2-(methacryloyloxy)ethyl 2-(dimethyldodecylammonio)ethyl phosphate, 4.1 parts of azobisisobutyronitrile, and 900 parts of n-butanol were introduced into a reactor fitted with a condenser, stirrer, thermometer, and nitrogen inlet tube and bubbling with nitrogen was carried out for 30 minutes. The obtained reaction mixture was heated for 8 hours at 65° C. under a nitrogen atmosphere to complete the polymerization reaction. The reaction solution was cooled to room temperature and the solvent was then distilled out under reduced pressure. The obtained residue was dissolved in chloroform and a dialytic purification was carried out using a dialysis membrane (Spectra/Por7 MWCO 1 kDa, Spectrum Laboratories, Inc.). The solvent was then distilled out under reduced pressure followed by drying under reduced pressure at 0.1 kPa or less at a temperature of 50° C. to obtain the polymer compound a.

The obtained polymer compound a was confirmed to have a weight-average molecular weight (Mw) of 12,300.

In Example 13 and Comparative Examples 3 and 4, CELLOXIDE CEL 2021P (Daicel Corporation, 3',4'-epoxycyclohexylmethyl 3,4-epoxycyclohexanecarboxylate) was used as an epoxide in place of the dodecyl vinyl ether and cyclohexanedimethanol divinyl ether.

In Example 14 and Comparative Examples 5 and 6, ARON OXETANE OXT-221 (Toagosei Co., Ltd., 3-ethyl-3-{[3-ethyloxetane-3-yl)methoxy]methyl}oxetane) was used as an oxetane in place of the dodecyl vinyl ether and cyclohexanedimethanol divinyl ether.

In Comparative Examples 2, 4, 6, 9, 10, 11, and 12, lecithin (Tokyo Chemical Industry Co., Ltd., soy derived) was used in place of the hydrogenated lecithin (LECINOL S-10EX, Nikko Chemicals Co., Ltd.) [compound 1].

In Examples 8 to 19, borobis(1,1-diphenyl-1-oxoacetyl) potassium salt (LR-147 (product name), from Japan Carlit Co., Ltd.) was used in place of the LIPIDURE (registered trademark)-S (polymer compound 3).

The same evaluations as in Example 1 were carried out on the resulting liquid developers. The results of these evaluations are given in Tables 1 and 2.

[Table 1] Evaluation results for ultraviolet-curable liquid developers

TABLE 1-1

| Example No. | compound 1 with formula (1) type | content | carrier liquid type | content ratio | type | content ratio | application of shear force? | heating? | polymer compound or charge control agent type | content | compound 1:polymer compound content ratio on a molar basis |
|---|---|---|---|---|---|---|---|---|---|---|---|
| Example 1 | Lecinol S-10EX | 1.50 | A-3 | 90 | A-17 | 10 | yes | yes | Lipidure-S | 0.50 | 7:1 |
| Example 2 | Basis LS-60HR | 1.50 | A-3 | 90 | A-17 | 10 | yes | yes | Lipidure-S | 0.50 | 7:1 |
| Example 3 | Basis LS-60HR | 1.50 | A-3 | 90 | A-17 | 10 | no | no | Lipidure-S | 0.50 | 7:1 |
| Example 4 | Basis LS-60HR | 1.50 | A-3 | 90 | A-17 | 10 | no | no | Lipidure-S | 0.10 | 35:1 |
| Example 5 | Basis LS-60HR | 1.50 | A-3 | 90 | A-17 | 10 | no | no | Lipidure-S | 0.05 | 70:1 |
| Example 6 | Basis LS-60HR | 1.50 | A-3 | 90 | A-17 | 10 | no | no | Lipidure-S | 1.00 | 3.5:1 |
| Example 7 | Basis LS-60HR | 1.50 | A-3 | 90 | A-17 | 10 | no | no | polymer compound a | 1.00 | 0.9:1 |
| Example 8 | Basis LS-60HR | 1.50 | A-3 | 90 | A-17 | 10 | no | no | LR-147 | 1.00 | — |
| Example 9 | Basis LS-60HR | 0.50 | A-3 | 90 | A-17 | 10 | no | no | LR-147 | 1.00 | — |
| Example 10 | Basis LS-60HR | 5.00 | A-3 | 90 | A-17 | 10 | no | no | LR-147 | 1.00 | — |
| Example 11 | Basis LS-60HR | 6.00 | A-3 | 90 | A-17 | 10 | no | no | LR-147 | 1.00 | — |

TABLE 1-1-continued

| Example No. | compound 1 with formula (1) type | content | carrier liquid type | content ratio | type | content ratio | application of shear force? | heating? | polymer compound or charge control agent type | content | compound 1:polymer compound content ratio on a molar basis |
|---|---|---|---|---|---|---|---|---|---|---|---|
| Example 12 | Basis LS-60HR | 0.30 | A-3 | 90 | A-17 | 10 | no | no | LR-147 | 1.00 | — |
| Example 13 | Basis LS-60HR | 0.30 | CEL 2021P | 100 | — | — | no | no | LR-147 | 1.00 | — |
| Example 14 | Basis LS-60HR | 0.30 | OXT-221 | 100 | — | — | no | no | LR-147 | 1.00 | — |
| Example 20 | Basis LS-60HR | 1.50 | A-3 | 90 | A-17 | 10 | no | no | no addition | — | — |
| Comparative Example 1 | no addition | — | A-3 | 90 | A-17 | 10 | no | no | no addition | — | — |
| Comparative Example 2 | lecithin (soy derived) | 1.50 | A-3 | 90 | A-17 | 10 | no | no | no addition | — | — |
| Comparative Example 3 | no addition | — | CEL 2021P | 100 | — | — | no | no | no addition | — | — |
| Comparative Example 4 | lecithin (soy derived) | 1.50 | CEL 2021P | 100 | — | — | no | no | no addition | — | — |
| Comparative Example 5 | no addition | — | OXT-221 | 100 | — | — | no | no | no addition | — | — |
| Comparative Example 6 | lecithin (soy derived) | 1.50 | OXT-221 | 100 | — | — | no | no | no addition | — | — |

The content is given in the table as the content (mass parts) per 100 mass parts of the toner particle.
The content ratio for the carrier liquid is given in the table on a mass basis.

TABLE 1-2

| Example No. | electrophoretic mobility | volume resistivity | developing performance | redispersibility | ultraviolet fixing performance |
|---|---|---|---|---|---|
| Example 1 | 10 | 10 | 10 | 10 | 10 |
| Example 2 | 10 | 10 | 10 | 10 | 10 |
| Example 3 | 9 | 10 | 9 | 9 | 10 |
| Example 4 | 9 | 10 | 9 | 9 | 10 |
| Example 5 | 8 | 10 | 8 | 9 | 10 |
| Example 6 | 9 | 9 | 9 | 9 | 9 |
| Example 7 | 8 | 9 | 8 | 7 | 9 |
| Example 8 | 7 | 9 | 7 | 7 | 9 |
| Example 9 | 7 | 9 | 7 | 7 | 9 |
| Example 10 | 7 | 9 | 7 | 7 | 9 |
| Example 11 | 7 | 8 | 6 | 7 | 9 |
| Example 12 | 6 | 9 | 6 | 7 | 9 |
| Example 13 | 6 | 5 | 6 | 7 | 7 |
| Example 14 | 6 | 5 | 6 | 7 | 7 |
| Example 20 | 8 | 10 | 7 | 7 | 10 |
| Comparative Example 1 | 2 | 10 | 2 | 2 | 10 |
| Comparative Example 2 | 4 | 2 | 4 | 4 | 2 |
| Comparative Example 3 | 2 | 9 | 2 | 2 | 9 |
| Comparative Example 4 | 4 | 1 | 4 | 4 | 1 |
| Comparative Example 5 | 2 | 9 | 2 | 2 | 9 |
| Comparative Example 6 | 4 | 1 | 4 | 4 | 1 |

TABLE 2

Evaluation results for liquid developers (not ultraviolet curable)

| Example No. | compound 1 with formula (1) type | content | carrier liquid type | content ratio | application of shear force? | heating? | charge control agent type | content | electrophoretic mobility | volume resistivity | developing performance | redispersibility |
|---|---|---|---|---|---|---|---|---|---|---|---|---|
| Example 15 | Lecinol S-10EX | 1.50 | MT-30P | 100 | yes | yes | LR-147 | 1.00 | 8 | 9 | 8 | 9 |
| Example 16 | Basis LS-60HR | 1.50 | MT-30P | 100 | yes | yes | LR-147 | 1.00 | 8 | 9 | 8 | 9 |
| Example 17 | Basis LS-60HR | 1.50 | MT-30P | 100 | yes | no | LR-147 | 1.00 | 7 | 9 | 7 | 8 |
| Example 18 | Basis LS-60HR | 1.50 | MT-30P | 100 | no | yes | LR-147 | 1.00 | 7 | 9 | 7 | 8 |
| Example 19 | Basis LS-60HR | 1.50 | MT-30P | 100 | no | no | LR-147 | 1.00 | 6 | 9 | 6 | 7 |

TABLE 2-continued

Evaluation results for liquid developers (not ultraviolet curable)

| Example No. | compound 1 with formula (1) type | compound 1 with formula (1) content | carrier liquid type | carrier liquid content ratio | application of shear force? | heating? | charge control agent type | charge control agent content | electrophoretic mobility | volume resistivity | developing performance | redispersibility |
|---|---|---|---|---|---|---|---|---|---|---|---|---|
| Comparative Example 7 | no addition | — | MT-30P | 100 | no | no | no addition | — | 2 | 10 | 2 | 2 |
| Comparative Example 8 | no addition | — | MT-30P | 100 | yes | yes | no addition | — | 2 | 10 | 2 | 2 |
| Comparative Example 9 | lecithin (soy derived) | 1.50 | MT-30P | 100 | no | no | no addition | — | 4 | 2 | 4 | 4 |
| Comparative Example 11 | lecithin (soy derived) | 1.50 | MT-30P | 100 | no | no | LR-147 | 1.00 | 5 | 1 | 4 | 4 |
| Comparative Example 10 | lecithin (soy derived) | 1.50 | MT-30P | 100 | yes | yes | no addition | — | 4 | 2 | 4 | 4 |
| Comparative Example 12 | lecithin (soy derived) | 1.50 | MT-30P | 100 | yes | yes | LR-147 | 1.00 | 5 | 1 | 4 | 4 |

The content is given in the table as the content (mass parts) per 100 mass parts of the toner particle.
The content ratio for the carrier liquid is given in the table on a mass basis.

The results in Table 1 and Table 2 demonstrate that the prior art Comparative Examples 2, 4, 6, 9, 10, 11, and 12 have a low electrophoretic mobility and a low volume resistivity and an inferior developing performance and an inferior redispersibility.

In contrast to this, Example 1 of the present invention is shown to provide a good electrophoretic mobility, volume resistivity, developing performance, and redispersibility.

A comparison of Example 2 with Example 3 shows that a better electrophoretic mobility, developing performance, and redispersibility are obtained through the execution of the application of shear and/or the execution of a heat treatment.

Moreover, a comparison of Example 5 with Examples 3 and 4 demonstrates that a better electrophoretic mobility and developing performance are obtained by using the range of 5:1 to 35:1 for the content ratio on a molar basis of the compound with formula (1) to the polymer compound having a structural unit with formula (2) [compound with formula (1): polymer compound having a structural unit with formula (2)].

A comparison of Example 6 with Examples 7 to 12 demonstrates that a better electrophoretic mobility, developing performance, and redispersibility are obtained when the polymer compound having a structural unit with formula (2) corresponds to a polymer compound 3.

In addition, a comparison of Example 7 with Examples 8 to 12 demonstrates that a better electrophoretic mobility and developing performance are obtained by the incorporation of a polymer compound having the structural unit with formula (2).

A comparison of Examples 8, 9, and 10 with Examples 11 and 12 demonstrates that a better developing performance is obtained by having the content of compound 1 be at least 0.50 mass parts and not more than 5.00 mass parts per 100 mass parts of the toner particle.

A comparison of Example 12 with Examples 13 and 14 demonstrates that a better volume resistivity and ultraviolet fixing performance are obtained by having the liquid cationically polymerizable compound be a vinyl ether compound.

However, in Example 19, scattered particles of the Basis LS-60HR were seen in the liquid developer and some unevenness and blank spots were seen when the image area was inspected with a light microscope post-fixing, but this was at a level where the unevenness and blank spots were almost undetectable by visual inspection.

INDUSTRIAL APPLICABILITY

The use of the liquid developer of the present invention makes it possible to reuse the liquid developer and to realize higher process speeds while obtaining a high image density and suppressing the occurrence of image blurring.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a national phase of PCT Application No. PCT/JP2016/066516, filed May 27, 2016, which in turn claims the benefit of Japanese Patent Application No. 2015-107395, filed May 27, 2015, which is hereby incorporated by reference herein in their entirety.

The invention claimed is:
1. A liquid developer comprising:
a carrier liquid;
a toner particle that is insoluble in the carrier liquid;
a compound with formula (1)

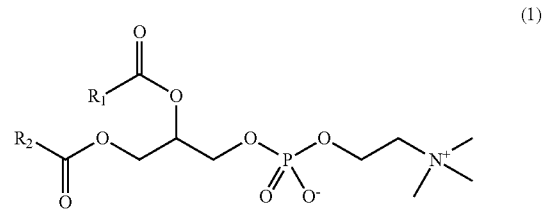

(1)

where $R_1$ and $R_2$ each independently represent an alkyl group having 13 to 23 carbons; and
a polymer compound that has a structural unit with formula (2)

(2)

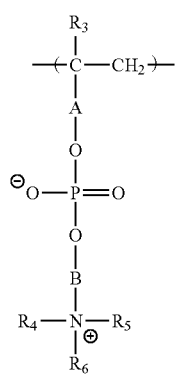

where $R_3$ to $R_6$ each independently represent a hydrogen atom or an alkyl group; A represents any of a single bond, carbonyl group, alkylene group, arylene group, or —COOR$_9$— (where the carbonyl group in —COOR$_9$— is bonded to a carbon atom to which $R_3$ is bonded and $R_9$ represents an alkylene having 1 to 4 carbons); and B represents an alkylene group or an arylene group, wherein the content ratio on a molar basis of the compound with formula (1) to the polymer compound having the structural unit with formula (2) is 5:1 to 35:1.

2. The liquid developer according to claim 1, wherein the carrier liquid contains a liquid cationically polymerizable compound.

3. The liquid developer according to claim 2, wherein the carrier liquid contains a vinyl ether compound.

4. The liquid developer according to claim 3, wherein the content of the compound with formula (1) in the liquid developer is 0.50 to 5.00 mass parts per 100 mass parts of the toner particle.

5. The liquid developer according to claim 4 wherein the polymer compound is formed of a copolymer that has the structural unit with formula (2) and a structural unit with formula (3)

(3)

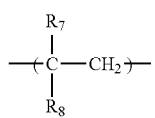

where $R_7$ represents either a hydrogen atom or an alkyl group, and $R_8$ is any of an alkyl group, carboxylate ester group, carboxamide group, alkoxy group, or aryl group.

6. The liquid developer according to claim 3, wherein the polymer compound is formed of a copolymer that has the structural unit with formula (2) and a structural unit with formula (3)

(3)

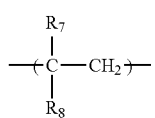

where $R_7$ represents either a hydrogen atom or an alkyl group, and $R_8$ is any of an alkyl group, carboxylate ester group, carboxamide group, alkoxy group, or aryl group.

7. The liquid developer according to claim 2, wherein the content of the compound with formula (1) in the liquid developer is 0.50 to 5.00 mass parts per 100 mass parts of the toner particle.

8. The liquid developer according to claim 7, wherein the polymer compound is formed of a copolymer that has the structural unit with formula (2) and a structural unit with formula (3)

(3)

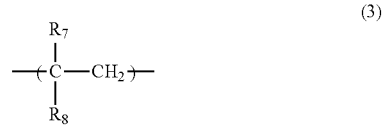

where $R_7$ represents either a hydrogen atom or an alkyl group, and $R_8$ is any of an alkyl group, carboxylate ester group, carboxamide group, alkoxy group, or aryl group.

9. The liquid developer according to claim 2, wherein the polymer compound is formed of a copolymer that has the structural unit with formula (2) and a structural unit with formula (3)

(3)

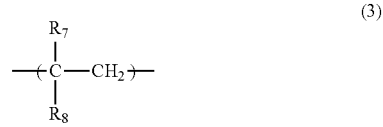

where $R_7$ represents either a hydrogen atom or an alkyl group, and $R_8$ is any of an alkyl group, carboxylate ester group, carboxamide group, alkoxy group, or aryl group.

10. The liquid developer according to claim 1, wherein the carrier liquid contains a vinyl ether compound.

11. The liquid developer according to claim 10, wherein the content of the compound with formula (1) in the liquid developer is 0.50 to 5.00 mass parts per 100 mass parts of the toner particle.

12. The liquid developer according to claim 11, wherein the polymer compound is formed of a copolymer that has the structural unit with formula (2) and a structural unit with formula (3)

(3)

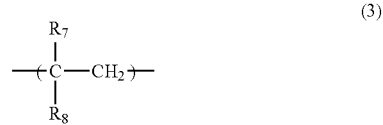

where $R_7$ represents either a hydrogen atom or an alkyl group, and $R_8$ is any of an alkyl group, carboxylate ester group, carboxamide group, alkoxy group, or aryl group.

13. The liquid developer according to claim 10, wherein the polymer compound is formed of a copolymer that has the structural unit with formula (2) and a structural unit with formula (3)

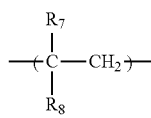

(3)

where $R_7$ represents either a hydrogen atom or an alkyl group, and $R_8$ is any of an alkyl group, carboxylate ester group, carboxamide group, alkoxy group, or aryl group.

14. The liquid developer according to claim 1, wherein the content of the compound with formula (1) in the liquid developer is 0.50 to 5.00 mass parts per 100 mass parts of the toner particle.

15. The liquid developer according to claim 14, wherein the polymer compound is formed of a copolymer that has the structural unit with formula (2) and a structural unit with formula (3)

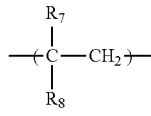

(3)

where $R_7$ represents either a hydrogen atom or an alkyl group, and $R_8$ is any of an alkyl group, carboxylate ester group, carboxamide group, alkoxy group, or aryl group.

16. The liquid developer according to claim 1, wherein the polymer compound is formed of a copolymer that has the structural unit with formula (2) and a structural unit with formula (3)

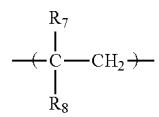

(3)

where $R_7$ represents either a hydrogen atom or an alkyl group, and $R_8$ is any of an alkyl group, carboxylate ester group, carboxamide group, alkoxy group, or aryl group.

17. A method of producing the liquid developer according to claim 1, comprising a step of:
applying a shear force and/or applying a heat treatment to a mixture in which the carrier liquid, the toner particle that is insoluble in the carrier liquid, and the compound with formula (1) are mixed.

* * * * *